US012653396B2

(12) United States Patent
Daye

(10) Patent No.: US 12,653,396 B2
(45) Date of Patent: Jun. 16, 2026

(54) VISION DEVICE FOR DETECTING EYE MOVEMENT

(71) Applicant: P³LAB, Céroux-Mousty (BE)

(72) Inventor: Pierre Martin Jack Gérard Daye, Braine-l'alleud (BE)

(73) Assignee: P³LAB, Céroux-Mousty (BE)

( * ) Notice: Subject to any disclaimer, the term of this patent is extended or adjusted under 35 U.S.C. 154(b) by 297 days.

(21) Appl. No.: 18/292,302

(22) PCT Filed: Jul. 20, 2022

(86) PCT No.: PCT/EP2022/070419
§ 371 (c)(1),
(2) Date: Jan. 25, 2024

(87) PCT Pub. No.: WO2023/006557
PCT Pub. Date: Feb. 2, 2023

(65) Prior Publication Data
US 2024/0215821 A1      Jul. 4, 2024

(30) Foreign Application Priority Data

Jul. 26, 2021      (BE) .................................... 2021/5575

(51) Int. Cl.
*A61B 3/113*          (2006.01)
*A61B 3/00*           (2006.01)
*A61B 3/15*           (2006.01)
(52) U.S. Cl.
CPC .............. *A61B 3/113* (2013.01); *A61B 3/005* (2013.01); *A61B 3/156* (2013.01)

(58) Field of Classification Search
None
See application file for complete search history.

(56) References Cited

U.S. PATENT DOCUMENTS 7,575,321 B2 * 8/2009 Newman ............... G01T 1/2985
                                                        351/205
9,039,632 B2 * 5/2015 Kiderman ................ A61B 5/16
                                                        600/558

(Continued)

FOREIGN PATENT DOCUMENTS

WO          2016007124 A1      1/2016
WO          2021022028 A1      2/2021

OTHER PUBLICATIONS

International Search Report with English Translation and Written Opinion for PCT Application No. PCT/EP2022/070419, dated Oct. 17, 2022, 11 pages.

*Primary Examiner* — Robert E. Tallman
(74) *Attorney, Agent, or Firm* — Dickinson Wright PLLC

(57) ABSTRACT

The disclosure relates to a vision device for detecting eye movement, which comprises a screen for displaying stimuli, an LCD panel for selectively blocking the viewing by either eye of the stimuli displayed on the screen, the panel being capable of adopting a number of configurations, including a configuration blocking the vision of either eye and a configuration allowing the vision of either eye, and at least one camera for tracking eye movement in wavelengths outside the visible spectrum through the panel. The camera being capable of tracking the movement of the eyes under the effect of the stimuli in the configurations of the panel that allow vision and block vision.

15 Claims, 1 Drawing Sheet

(56) References Cited

U.S. PATENT DOCUMENTS

| | | | |
|---|---|---|---|
| 10,488,920 B2 * | 11/2019 | Lin | G06V 40/193 |
| 10,606,349 B1 * | 3/2020 | Ouderkirk | G06T 7/20 |
| 2015/0223683 A1 | 8/2015 | Davidovics et al. | |
| 2016/0000317 A1 * | 1/2016 | Krall | A61B 3/08 |
| | | | 351/240 |
| 2017/0150882 A1 * | 6/2017 | Lindig | A61B 3/005 |
| 2019/0385342 A1 | 12/2019 | Freeman et al. | |
| 2020/0146546 A1 | 5/2020 | Chene et al. | |
| 2020/0397288 A1 * | 12/2020 | Zidan | G02B 27/0093 |

* cited by examiner

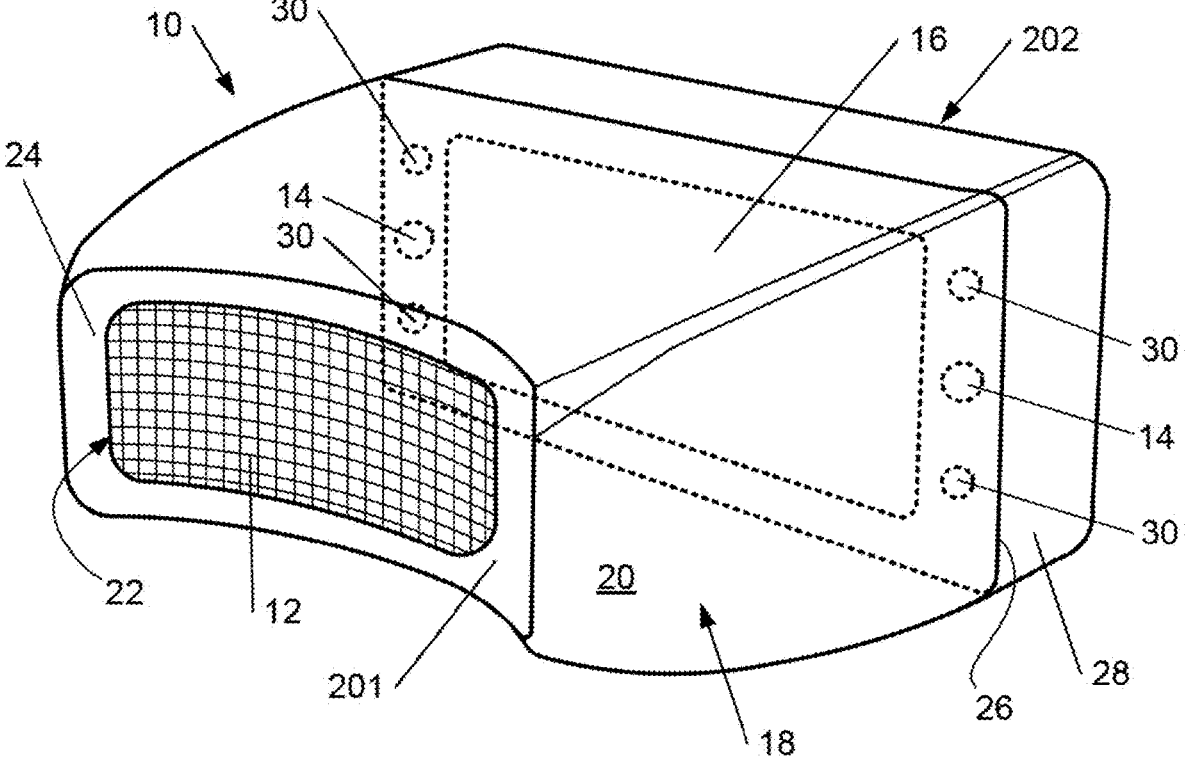

VISION DEVICE FOR DETECTING EYE MOVEMENT

CROSS-REFERENCE TO RELATED APPLICATION(S)

This present application is a national stage application of International Patent Application No. PCT/EP2022/070419, filed Jul. 20, 2022, which claims priority to Belgium Patent Application No. 2021/5575, filed Jul. 26, 2021, the disclosures of which are hereby incorporated by reference in their entireties.

TECHNICAL FIELD

The present disclosure relates to a vision device for detecting eye movement.

BACKGROUND

The disclosure relates to the field of the eye movement detection under the effect of visual stimuli. This may involve the identification of ocular disorders and/or neurological disorders, as well as the re-education of the disorders of the vision through the analysis of the movements of the eyes of a patient. It may also involve the detection of the eye movement in the virtual reality.

When the movements of the eyes are detected under the effect of visual stimuli, it is possible to selectively block the vision in one eye (for example for a medical analysis or when presenting 3D stimuli). However, when the vision of one eye is blocked—by an opaque screen, for example—it is no longer possible to detect the movements of that eye.

There is therefore a need for a device allowing to detect the movements of an eye under the effect of stimuli, even when the vision of that eye is blocked.

SUMMARY

To this end, the disclosure proposes a vision device for detecting eye movement comprising an LCD panel for selectively blocking the vision of one eye and/or the other, the panel being able to be in several configurations, including a configuration blocking the vision of one eye and/or the other and a configuration allowing the vision of one eye and/or the other. The device also comprises at least one camera for tracking the eye movement in the wavelengths outside the visible spectrum through the panel, the camera being able to track the eye movement in configurations of the panel allowing the vision and blocking the vision.

More specifically, the disclosure proposes a vision device for detecting eye movement comprising a screen for displaying stimuli, an LCD panel for selectively blocking the vision of one eye and/or the other of the stimuli displayed on the screen, the panel being able to be in several configurations, including a configuration blocking the vision of one eye and/or the other and a configuration allowing the vision of one eye and/or the other. The device also comprises at least one camera for tracking the eye movement in the wavelengths outside the visible spectrum through the panel, the camera being able to track the eye movement under stimuli in configurations of the panel allowing the vision and blocking the vision.

In one embodiment, the wavelengths are those of the infrared.

In one embodiment, the device also comprises emitters for illuminating the panel in the infrared wavelengths.

In one embodiment, the panel comprises at least one LCD area per eye.

In one embodiment, the panel is continuous for both eyes, the panel comprising pixels selectively blocked for the vision of one eye or the other.

In one embodiment, the panel comprises pixels associated with a colour filter, the pixels being selectively blocked.

In one embodiment, the device comprises a vision cone with a chamber having a first end and a second end, a processing unit at one end of the chamber, the processing unit comprising the screen for displaying the visual stimuli and the camera or cameras for tracking the eye movement, an opening at the other end of the chamber for the vision of the visual stimuli on the display screen, the camera or cameras being able to track the eye movement through the panel in configurations allowing the vision and blocking the vision.

In one variant, the configuration of the panel is controlled by the processing unit.

In one variant, the panel is removably positioned in the cone of vision.

In one variant, the device comprises at least one camera filming both eyes.

In one variant, the screen provides backlighting for the panel.

The use of the verb "comprise", its variants and conjugations in this document in no way precludes the presence of elements other than those mentioned. The use in this document of the indefinite article "a", "an", or the definite article "the" to introduce an element does not exclude the presence of a plurality of these elements.

The terms "first", "second", etc. are used in this document exclusively to differentiate between different elements, without implying any order between them.

The various embodiments can be considered individually or in combination.

BRIEF DESCRIPTION OF THE FIGURES

Further characteristics and advantages of the present disclosure will become apparent from the following detailed description, for the understanding of which reference is made to the appended FIGURE showing:

FIG. 1 shows the device according to one example of embodiment of the disclosure.

The drawing of the FIGURE is not to scale. Similar elements are generally denoted by similar references in the figures. For the purposes of this document, the identical or similar items may bear the same references. Furthermore, the presence of reference numbers or letters in the drawings cannot be regarded as limiting, even when these numbers or letters are indicated in the claims.

DETAILED DESCRIPTION

The disclosure relates to a vision device for detecting eye movement comprising a screen for displaying stimuli and an LCD panel for selectively blocking the vision of one eye and/or the other from stimuli displayed on the screen, the LCD panel being able to be in a plurality of configurations, including a configuration blocking the vision of one eye and/or the other and a configuration allowing the vision of one eye and/or the other. The device also comprises at least one camera for tracking the eye movement in the wavelengths outside the visible spectrum through the LCD panel, the camera being able to track the eye movement under stimuli in configurations of the LCD panel allowing the vision and blocking the vision. Such a device allow to detect the movements of an eye under the effect of stimuli, even when the vision of that eye is blocked. This offers the advantage of being able to take measurements throughout the exercise on the eyes whose vision is blocked or allowed.

FIG. 1 illustrates the device 10 according to one example of embodiment of the disclosure. The device 10 is used to detect the eye movement under the effect of visual stimuli. This may involve the identification of ocular disorders and/or neurological disorders, as well as the rehabilitation of the disorders of the vision through the analysis of the movement of the eyes of a user. For example, the device allows to present a visual stimulus monocularly (hiding one eye when the stimulus is presented) while recording the hidden eye. This allows to study a strabismus or a deviation in the position of the two eyes without being influenced by the image fusion mechanisms or having to ask the user for perceptive feedback (as in the Hess Lancaster test). The device can also be used to detect the eye movement in the virtual reality.

The device 10 may comprise a panel 12 for selectively blocking the vision of one eye and/or the other of a user. The panel 12 can be configured in a number of configurations. In one configuration, the vision of one eye or of the other of the user is blocked; this allows the other eye to react to the visual stimuli. In another configuration, the vision of one eye or the other is allowed; this allows that eye to react to stimuli. Other configurations can also be envisaged, for example in which the vision of both eyes is blocked (other stimuli can be applied) or the vision of both eyes is allowed or the vision of one eye and/or the other is darkened or the visual inputs are filtered by a colour displayed by the LCD panel, etc. The panel 12 allows a wide range of configurations for working the eyes under different conditions and thus making a variety of measurements.

The panel 12, for example, is an LCD (acronym for Liquid Crystal Display). The panel 12 consists, for example, of a layer of liquid crystals placed between two electrodes. A light source described in more detail later can provide a backlight, being placed on the other side of the panel 12 relative to the user. Depending on whether a voltage is applied to the electrodes, the configuration (in particular the orientation) of the liquid crystals remains stable or is modified, allowing light to pass through or be blocked—and therefore allowing an image to be seen or not, or in other words, allowing the vision or blocking the vision. For example, the light can pass through the panel 12 if no voltage is applied to the liquid crystals between the electrodes; by applying a voltage to the electrodes and varying it, the liquid crystals rotate variably across the panel—or more specifically, across each pixel—thereby filtering the component of the light that can pass through. The applied voltage that determines the tilt of the liquid crystals thus modifies the brightness level of the panel—or of each pixel—and allows the light to be blocked or an image to be displayed in greyscale. In addition, the advantage of the LCD nature of the blocking panel is that the panel 12 is highly responsive to vision-blocking or vision-allowing instructions—making testing easier.

The device also comprises a stimuli display screen 16. The screen 16 is separate from the panel 12. The screen 16 displays stimuli which are followed by the eyes of the patient. The eyes of the patient are attentive to the stimuli displayed on the screen. The stimuli displayed on the screen generate movements in the eyes of the patient. The panel 12 selectively blocks the stimuli displayed by the screen 16. One of the configurations of the panel blocks the vision of one eye and/or of the other of the screen and another configuration allows vision of one eye and/or the other of the screen. In other words, one of the configurations of the panel blocks the vision of one eye and/or the other of the screen and another configuration allows vision of one eye and/or the other of the screen. In other words, one of the configurations of the panel blocks the vision of the screen of one eye and/or the other and another configuration allows the vision of the screen of one eye and/or the other.

The panel 12 selectively blocks the vision of one eye and/or the other to the stimuli displayed by the screen 16. In other words, the stimuli displayed by the screen 16 are selectively blocked by the panel 12, with one configuration of the panel blocking the stimuli displayed by the screen and another configuration of the panel allowing the vision of the stimuli displayed by the screen. Blocking the screen 16 with the blocking panel 12 allows to keep the stimuli in sequence and prevents the test from being distorted. Blocking the screen—rather than turning it off—also allows a different test to be applied to each eye, with the stimuli masked for one eye and maintained for the other. The blocking panel 12 allows to avoid switching the screen off and on again, which would hinder the test. Blocking the screen while the stimuli are displayed means that testing under the effect of stimuli can be carried out simply and efficiently. Furthermore, the advantage of the blocking panel 12 being separate from the screen is that the panel can be placed close to the eyes even though the screen is further away. This allows the eyes to be really blocked.

The device 10 may also comprise at least one tracking camera 14 for tracking the eye movement. The camera or the cameras 14 can record the eye movements in order to carry out analyses—either directly or after the eye movements have been recorded by processing the images of the videos recorded by the camera or cameras. The device 10 comprises at least one camera filming both eyes. This makes the device 10 less expensive. Preferably, the device 10 comprises two cameras; this allows one camera to be focused on each eye, thereby increasing the spatial resolution and the quality of the images recorded for each eye. The camera or cameras are positioned on the other side of the panel 12 relative to the user; the panel 12 is between the user and the camera or cameras 14.

The camera or cameras 14 are able to track the eye movement in the wavelengths outside the visible spectrum through the panel 12. The camera or cameras 14 are able to track the movement of the eyes in the configurations of the panel 12 allowing the vision and blocking the vision of the eyes. In this way, the device 10 allows a video of the eyes to be recorded through the panel 12 whatever the configuration of the panel 12; in particular, when the panel 12 is in a configuration blocking the vision of one eye, the camera or cameras 14 are able to record a video of the eye. This therefore allows the eye movements to be recorded continuously during the test period, through the panel 12 when it prevents the visible light from passing through the panel 12. During the test period, the vision of the eyes is allowed or blocked by the panel 12 by allowing or preventing the visible light to pass through in order to assess each eye under different visibility conditions, but the camera or cameras are able to film the eye movements in the wavelengths outside the visible spectrum.

The wavelengths of the spectrum visible to the human eye range from 400 nm to 800 nm. The panel 12 can selectively block the vision of either eye (or both) in this wavelength range. In this way, the device 10 comprising the screen 16 displaying stimuli allows the eyes to be exercised—selectively or otherwise. The screen 16 can be the light source along the visible length that provides the backlighting for the panel 12. In the configuration allowing the vision of one eye, the panel 12 allows the light from the screen 16 to pass to that eye; the eye is able to see the stimuli displayed on the screen 16. In the vision-blocking configuration for one eye, the panel 12 blocks the passage of the light from the screen 16 to that eye; the eye is unable to see the stimuli displayed on screen 16. The panel 12 can also be in intermediate configurations between blocking and allowing the vision— with grey levels. Whatever the configuration of the panel— and in particular in the vision blocking configuration—the camera or cameras 14 are able to track and record the eye movement outside the wavelengths of the visible spectrum.

The camera or cameras are able to track the movement of the eyes—and to film them—above and below the wavelengths of the spectrum visible to the human eye between 400 nm and 800 nm. In particular, the camera or cameras 14 are able to track the movement of the eyes in the infrared wavelengths. The camera or the cameras 14 are able to track the movement of the eyes in the wavelengths beyond the wavelengths visible to the human eye, for example above 800 nm, preferably above 900 nm, whatever the configuration of the panel 12. In this way, it is possible for the device 10 to record the eye movements through the opaque panel for the visible and to track the eye movements not subjected to the stimuli.

As shown in FIG. 1, the device 10 may comprise a vision cone 18 carrying the panel 12. The vision cone can be portable or stationary. The vision cone 18 may comprise a lateral wall delimiting a chamber 20 having a first end 201 and a second end 202. At the first end 201 of the chamber 20, the vision cone 18 comprises an opening 22 allowing a user to see inside the chamber 20 and more specifically, as will be described later, to see a processing unit at the second end 202. The opening 22 is circumscribed by a periphery 24 able to be in contact with the forehead of the user. In other words, the user presses the top of the periphery 24 of the opening 22 against his forehead so that his gaze enters the chamber 20 through the opening 22. The periphery 24 of the opening 22 can be flat but is preferably concave towards the inside of the chamber 20; this allows the periphery 24 to be well applied to the face of the user so that the cone 18 blocks the entry of light from the side of the eyes to make the inside of the chamber quite dark. The periphery 24 can also comprise a cavity (not visible in FIG. 1) to adapt the periphery 24 to the nose of the user.

At the second end 202 of the chamber, the cone 18 comprises an attachment interface 26 for attaching a processing unit 28. The processing unit 28 comprises the screen 16 for displaying visual stimuli and the camera or cameras 14 for tracking the eye movement. So, once the periphery 24 has been applied to the forehead of the user and surrounds his field of vision, the user can see the visual stimuli on the display screen 16 of the processing unit 28 through the opening 22.

The panel 12 is carried by the vision cone 18 so that the camera or cameras 14 are able to track the movement of the eyes attentive to the stimuli displayed on the screen 16, through the panel 12 and whatever the configuration of the panel, in particular the configurations allowing the vision and blocking the vision. The panel 12 is between the eyes of the user and the screen 16. The panel 12 can be positioned in different positions in the cone 18. For example, the cone 18 can comprise a slit in the wall defining the chamber 20, into which the panel 12 can be inserted. According to FIG. 1, the panel 12 can be positioned in the opening 22 of the cone 18; the advantage of this position is that the panel is as close as possible to the eyes of the user, to better block the vision of one eye in this configuration of the panel 12, without obstructing the vision of the other eye. The panel 12 can also be removably positioned in the cone of vision. This allows to choose whether or not to use the panel 12 for tests and exercises, or to change the panel 12.

The device 10 can comprise emitters 30 for illuminating the panel 12 in the operating wavelengths of the camera or cameras 14. These are preferably emitters 30 in the infrared wavelengths if the camera or cameras operate in this wavelength range—wavelengths greater than 800 nm, preferably greater than 940 nm—which are not visible to the human eye but allowing the eyes to be illuminated for the detection of the eye movement by the camera or cameras 14 through the panel 12.

The panel 12 can comprise at least one LCD area per eye. Each eye comprises an LCD-type panel area. This makes it easier to control each area of panel 12 to one configuration or another. The areas for each eye can be completely delimited, in the same way as a pair of glasses comprising two LCD panels. The panel 12 can also be continuous for both eyes, with the panel 12 comprising pixels that are selectively blocked for the vision of one eye or the other. This embodiment has the advantage of adapting better to the morphology of the user.

The panel 12 may comprise pixels associated with a colour filter, the pixels being selectively blocked. The panel 12 can thus modulate in colour, and it is possible to impose filtering of a colour seen by the user (for example red) while continuing to track the eye movements with the camera or cameras 14. This allows to provide a wider range of exercises for the user to practise, and in particular to test their reaction to colours.

The processing unit 28 allows the control of the operation of the device 10. In particular, the processing unit controls the configuration of the panel 12. The change from one configuration to another of the panel 12, in particular the change to the configuration allowing the vision or blocking the vision, is controlled by the processing unit 28. As the processing unit 28 also controls the screen 16 and in particular the display of visual stimuli, the processing unit 28 can therefore coordinate the display of stimuli and the configuration of the panel 12. This allows to record scenarios in the processing unit coordinating the display on the screen and the blocking/vision of each eye through the panel—for the identification of ocular disorders and/or neurological disorders as well as the rehabilitation of the disorders of the vision and the detection of the eye movement in the virtual reality.

The processing unit 28 controls the configuration of the panel, for example by varying the voltage applied to the electrodes of the panel. If the panel 12 comprises a single area common to both eyes or a delimited area specific to each eye, the control unit 28 controls the area or areas for each eye. The processing unit 28 can control the pixels of the panel to adapt to each eye.

The device allows to implement a method for detecting the eye movement. The method comprises displaying stimuli on the screen 16 and selectively blocking the vision of one eye and/or the other from the stimuli displayed on the screen 16. The method comprises the tracking of the eye movement by at least one camera 14 in the wavelengths outside the visible spectrum through the panel 12; the camera tracks the eye movement under the effect of stimuli in configurations of the panel 12 allowing the vision and blocking the vision. The method allows to detect the movements of an eye under the effect of stimuli, even when the vision of that eye is blocked. This offers the advantage of being able to take measurements throughout the exercise on the eyes whose vision is blocked or allowed. The device and the method allow the eye disorders and/or neurological disorders to be identified and the vision disorders to be rehabilitated by analysing the movement of the eyes of a patient.

The present disclosure has been described above in connection with specific embodiments, which are illustrative and should not be considered limiting. Generally speaking, it will be obvious to a person skilled in the art that the present disclosure is not limited to the examples illustrated and/or described above.

The invention claimed is:

1. A vision device for detecting eye movement comprising:
  a stimuli display screen;
  an LCD panel for selectively blocking vision of one eye or the other eye of stimuli displayed on the stimuli display screen, wherein the LCD panel is able to be in several configurations, including a configuration blocking the vision of one eye or the other eye and a configuration allowing the vision of one eye or the other eye; and
  at least one camera for tracking the movement of the eyes in wavelengths outside the visible spectrum through the LCD panel, wherein the at least one camera is able to track the movement of the eyes under an effect of the stimuli in the configurations of the LCD panel, allowing the vision and blocking the vision.

2. The vision device according to claim 1, wherein the wavelengths are those of infrared wavelengths.

3. The vision device according to claim 2, further comprising emitters for illuminating the LCD panel in the infrared wavelengths.

4. The vision device according to claim 1, wherein the LCD panel comprises at least one LCD area per eye.

5. The vision device according to claim 1, wherein:
  the LCD panel is continuous for both eyes; and
  the LCD panel comprises pixels selectively blocked for the vision of the one eye or the other eye.

6. The vision device according to claim 1, wherein:
  the LCD panel comprises pixels associated with a colour filter; and
  the pixels are selectively blocked.

7. The vision device according to claim 1, further comprising:
  a vision cone with a chamber having a first end and a second end;
  a processing unit at the first end of the chamber, the processing unit comprising the stimuli display screen for displaying stimuli and the at least one camera for tracking the eye movement; and
  an opening at the second end of the chamber for the vision of the stimuli on the stimuli display screen,
  the at least one camera being able to track the movement of the eyes through the LCD panel in configurations allowing the vision and blocking the vision.

8. The vision device according to claim 7, wherein the configuration of the LCD panel is controlled by the processing unit.

9. The vision device according to claim 7, wherein the LCD panel is removably positioned in the vision cone.

10. The vision device according to claim 7, the at least one camera is further configured to film both eyes.

11. The vision device according to claim 7, wherein the stimuli display screen provides backlighting for the LCD panel.

12. A method for detecting eye movement, comprising:
  providing a vision device, the vision device comprising:
    a stimuli display screen;
    an LCD panel for selectively blocking vision of one eye or the other eye of stimuli displayed on the stimuli display screen, the LCD panel being able to be in several configurations, including a configuration blocking the vision of one eye or the other eye and a configuration allowing the vision of one eye or the other eye; and
    at least one camera for tracking the movement of the eyes in wavelengths outside the visible spectrum through the LCD panel;
  displaying the stimuli on the stimuli display screen;
  selectively blocking the vision of one eye or the other eye from the stimuli displayed on the stimuli display screen; and
  tracking of the eye movement by the at least one camera in the wavelengths outside the visible spectrum through the LCD panel, wherein:
    the at least one camera tracks the eye movement under an effect of the stimuli in configurations of the LCD panel; and
    the tracking of the eye movement causes the allowing the vision of the one eye or the blocking the vision of the one eye.

13. The method according to claim 12, the vision device further comprising:
  a vision cone with a chamber having a first end and a second end; and
  a processing unit at one end of the chamber, wherein:
    the processing unit comprises the stimuli display screen for displaying the stimuli and the at least one camera for the tracking the eye movement; and
    the processing unit controls the display of the stimuli on the stimuli display screen and coordinates the display of the stimuli and the configuration of the LCD panel.

14. The method according to claim 13, further comprising recording scenarios in the processing unit that coordinates a display on the stimuli display screen and allows the vision and blocks the vision of each eye through the LCD panel.

15. The method according to claim 12, wherein the configurations of the LCD panel allowing the vision and blocking the vision are different for each eye.

\* \* \* \* \*